United States Patent [19]
Cohen

[11] Patent Number: 5,207,712
[45] Date of Patent: May 4, 1993

[54] ABSORBABLE JOINT IMPLANTS FOR THE LESSER DIGITS AND METATARSAL PHALANGEAL JOINTS IN THE SURGICAL CORRECTION OF THE FOOT

[76] Inventor: Michael Cohen, 170 Lakeview Dr. #201, Ft. Lauderdale, Fla. 33326

[21] Appl. No.: 879,886

[22] Filed: May 7, 1992

[51] Int. Cl.$^5$ ............................................. A61F 2/42
[52] U.S. Cl. ...................................... 623/21; 606/59; 606/60; 606/72; 606/76
[58] Field of Search ............... 623/21, 18, 16; 606/59, 606/60, 62, 72, 76, 77

[56] References Cited

U.S. PATENT DOCUMENTS

| | | | |
|---|---|---|---|
| 4,634,445 | 1/1987 | Helal | 623/21 |
| 4,858,603 | 8/1989 | Clemow et al. | 606/77 |
| 4,898,186 | 2/1990 | Ikada et al. | 606/62 |
| 4,969,909 | 11/1990 | Barouk | 623/21 |
| 5,092,896 | 3/1992 | Meuli et al. | 623/21 |

OTHER PUBLICATIONS

Shaw H. Alan, Alvarez Gregory, *The Use of Digital Implants for the Correction of Hammertoe Deformity and Their Potential Complications and Management*, 31 The Journal of Foot Surgery, No. 1 pp. 63–74 (Jan./Feb. 1992).
*A Totally Absorbing Disappearing Act !*, OrthoSorb absorbable pin advertisement, The Journal of Foot Surgery, ibid. at ii.
*Orthosorb Absorbable pin: Setting the Standard for Absorbable Internal Fixation for Shear or Torque Forces in the Foot, Hand, or Knee*, Handout literature distributed by Johnson & Johnson Orthopaedics (1991) 325 Paramount Dr., Raynham, Mass. 02767.
Gotkin, *Introducing the Absorbable Tapered Pins*, 1 Absorbable Update #2, pp. 1–3 (Jul./Aug. 1991 Boca Biomedical Inc.).
*Shear Strength . . . With a Fracture fixation pin that's gradually absorbed*, Johnson & Johnson Orthopaedics brochure (1990).
*BioAction Great Toe Implant*, Orthopaedic Biosystems advertisement.

Primary Examiner—Randall L. Green
Assistant Examiner—Mary Beth O. Jones
Attorney, Agent, or Firm—Nolte, Nolte & Hunter

[57] ABSTRACT

A method and apparatus for surgical correction of malformations of digits of a foot. Part of the joint is removed to expose bone ends. The bone ends are spaced apart from each other at a distance greater than would be suitable for knitting of said bone ends to each other with bone tissue. Holes are bored in each of the bone ends. An implant, including shafts and a central spacer, is inserted into each of the holes in the bones. This implant consists entirely of absorbable material. The implant is left permanently in place to be completely absorbed as it is replaced by fibrous scar tissue. This tissue forms an effective joint replacement.

10 Claims, 7 Drawing Sheets

ABSORBABLE JOINT IMPLANTS FOR THE LESSER DIGITS AND METATARSAL PHALANGEAL JOINTS IN THE SURGICAL CORRECTION OF THE FOOT

FIELD OF INVENTION

The present invention relates to methods and apparatus for the correction of malformations of the foot, and particularly to methods and apparatus for correction of hammer toes or similar conditions of the lesser digits and metatarsal phalangeal joints by surgical correction of the foot.

BACKGROUND OF INVENTION

To date, there exist various types of implant-joint replacement of the foot. Dow Corning Wright has manufactured the SILASTIC® HP 100 (Swanson type) Weil design, which consists of a double stemmed flexible implant with a cylindrical center body. Sutter Biomedical introduced both the Sutter and Sgarlato design which also consist of flexible double-hinged implants with a rectangular or trapazoidal central body. The techniques involved in implantation of these devices are rather similar. All consist of an arthroplasty of the joint, with resection of the head of the proximal phalanx, reaming of the modulary canal, and stem insertion. A description of these techniques is found in Shaw, A., et al. *The use of Digital Implants For the Correction of Hammer Toe Deformity and Their Potential Complications and Management*, 31 The Journal of Foot Surgery 63 (January/February 1992.)

Though simple, this technique is frought with complications. These include the following:
1. recurrence of FLEXION deformity;
2. infection;
3. biomaterial failure;
4. bone damage;
5. reactive synovitis with silicone shards discovered in inguinal nodes; and
6. implant dislocation..

BIODEGRADABLE BONE PINS

Presently there are numerous materials that are biodegradable in the human body. Polyglycolic acid is a material used in DEXON® (Davis & Geck) which is an absorable suture that is elimated by hydrolysis. The same material has been utilized as a fixation material for bone fragments. However, its rigidity and recent reports of foregin body reactions, make it a poor candidate for implant material.

Johnson & Johnson has introduced the ORTHOSORB® absorbable pin—tapered pin. It is made of the same material marketed by Johnson & Johnson as PDS®. The pin is constructed from poly-p-dioxanon, stained with D+C violet #2 to which a stainless steel K wire is attached. The pin is placed across a fracture site and is absorbed over a period of six months through hydrolysis. Healing ultimately takes place without resurgery to remove the fixation devices. In the placement of such pins, a usual object is to reduce the fracture fragments to a reasonable distance, which enables union to take place between the bones, rather than a gap being filled by fibrous tissue which would result across too large a gap. *Ortho Sorb* brochure (1990 Johnson & Johnson) illustrates such bone growth. This indicates that the absorbable device acts as a stabilization device rather than an onlay graft. As the pin is hydrolyzed, it is ultimately replaced by bone as the fracture heals.

See also U.S. Pat. No. 4,858,603, Bone Pin to Clemow, et al.

OBJECTS OF INVENTION

It is an object of this invention to avert most of the complications encountered with implantation of a foreign body.

It is a further object of this invention to create an implant which would:
1. be easy to implant;
2. have low possibilities of foreign body rejection;
3. stabilize the digit;
4. provide a framework in which scar tissue (fibrous tissue) can form;
5. last long enough for mature fibrous tissue to adequately replace it;
6. be relatively cost effective; and
7. ultimately be absrobed and replaced by said fibrous tissue.

BRIEF DESCRIPTION OF THE PRESENT INVENTION

The present invention would achieve these objects by providing a metatarsal implant of a biodegradable substance that would eventually be replaced by mature fibrous tissue.

It is a documented fact that once an implant has been in place for a period of six weeks, the full benefit of the implant has been achieved. (Shaw, et al, supra at 63.) Fibrous tissue that will stabilize the toe and serve to maintain digital length (the two major goals of digital implant surgery of the foot) is present and relatively mature.

Contrary to the teaching of the bone pin art, the present invention would involve an arthroplasty in which a gap of more than 1 mm. is left between bone sections on either side of the excised joint. A biodegradeable implant is inserted between the bone sections to locate the bone sections and maintain the distal spacing beyond that space which permits the growth of bone therebetween.

Over time, fibrous tissue forms around the implant, and replaces the implant, which is eventually absorbed into the body. This process usually takes 6-7 months through a process known as hydrolysis.

The implant may take a number of appropriate forms, as described below.

DETAILED DESCRIPTION OF THE DRAWINGS

The digital and metarso phalangeal joints would beneficially be constructed from Poly-p-dioxanon (the same material ORTHOSORB is constructed from), and would be similarly stained. Two designs would be introduced:

Type I—This would be used in a digit that requires a minimal amount of transverse plane and saggital plane stability.

Figure 1:
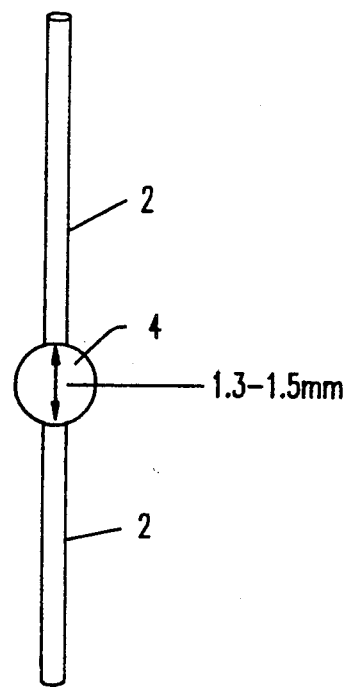
FIG. 1 is an elevation of one embodiment of the present invention.

FIG. 1 shows a solid rod 2 of approximately 1.0 mm diameter, comprising a solid 1.3-1.5 mm ball 4 in the center of the rod's longitudinal axis.

Figure 2:
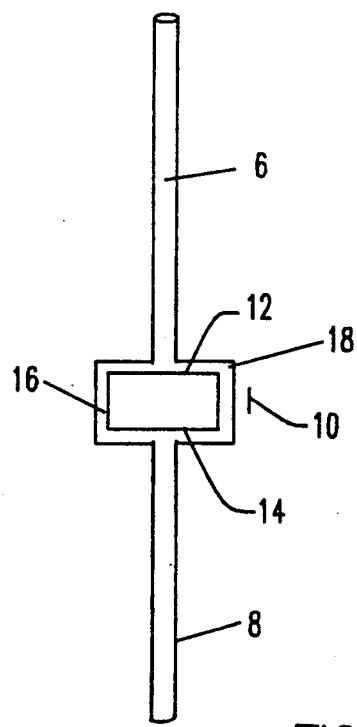
FIG. 2 is an elevation of a second embodiment of the present invention.

FIG. 2 shows a similar arrangement wherein shafts 6, 8 are connected and spaced by spacer 10 comprising two transverse pegs 12, 14 connected by longitudinal stabilizers 16, 18.

Figure 3:
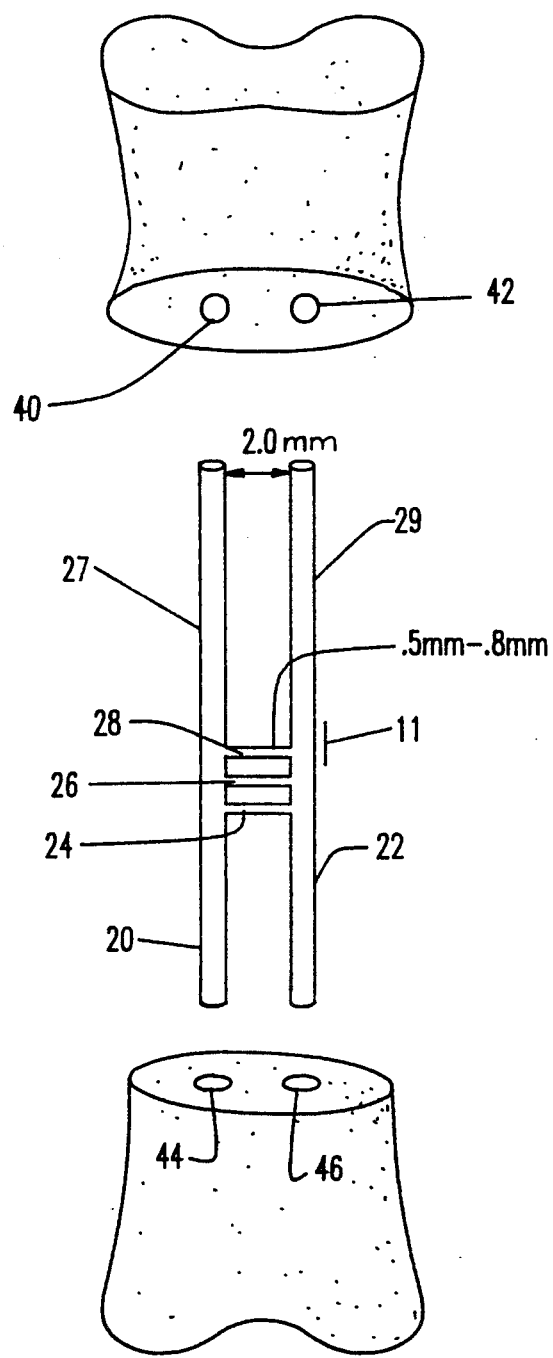
FIG. 3 is an exploded view showing a third embodiment of the present invention, located between bone ends into which this embodiment may be fitted.

Type II—As shown in FIG. 3, this type of implant 11 would be suitable for a digit or metarsarsal phalangeal joint requiring additional transverse and saggital plane stability. It comprises double 1 mm poly-P-dioxanon pins 6,8 with mid 15 mm connections 10 very much like a ladder. The ladder comprises a pair of 1 mm connections 10 20, 22 and transverse pegs 24, 26, 28 connected by longitudinal stabilizers 27, 29. Insertion technique must involve K-wire (Kirschner-wire) drilling of recipient bones, with use of templates for parallel drilling.

Pegs 24, 26, 28 have a diameter between 0.5 and 0.8 mm. The transverse pegs 24, 28 provide trans-sectional bone spacing between 1.5-1.8 mm. Spacing between shafts 20, 22 is about 2 mm.

Figure 4:
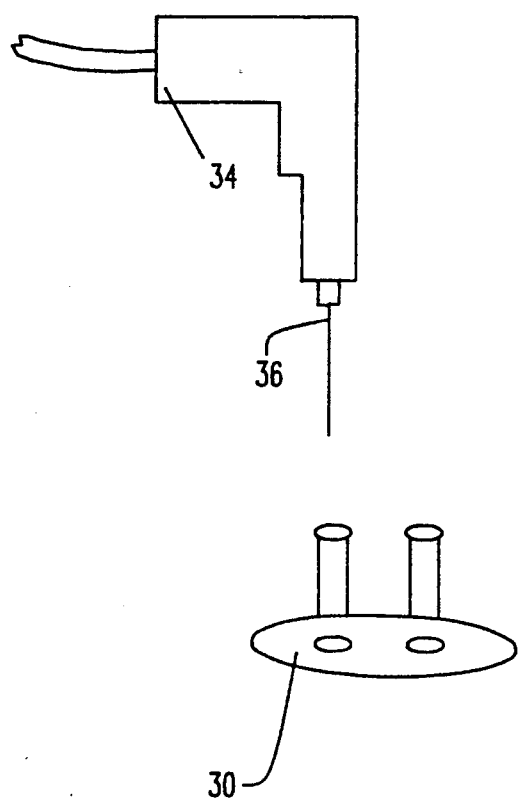
FIG. 4 is a view showing a drilling template and a drill driver with a K-wire bit.
Figure 5:
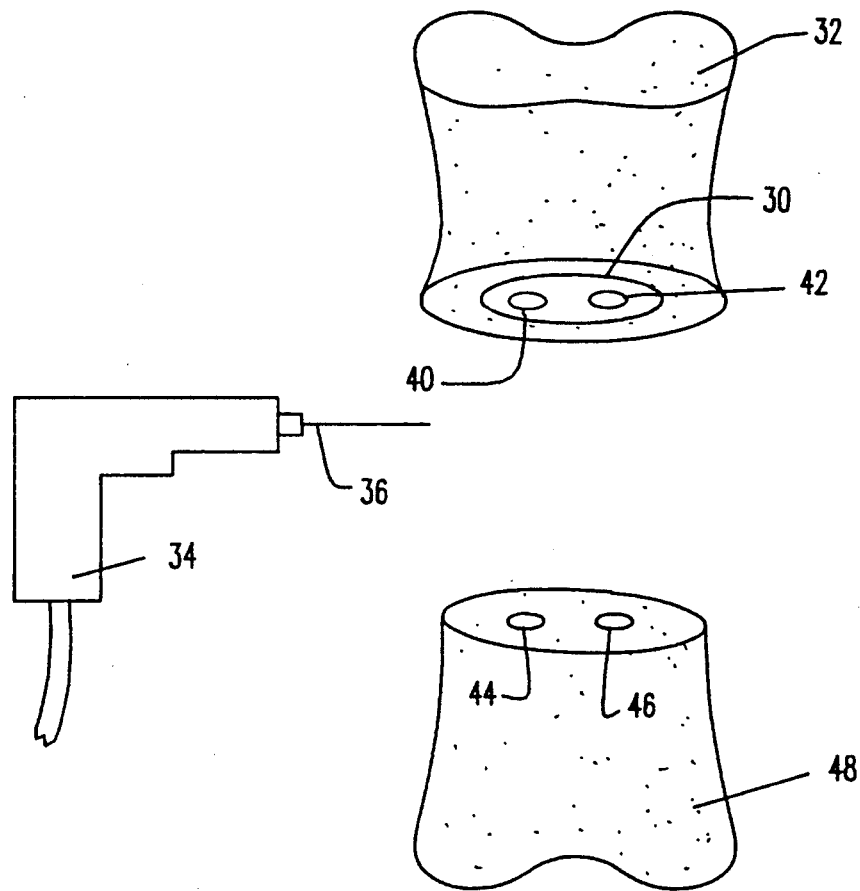
FIG. 5 is an elevation of a pair of bone ends with a template in place to be drilled.

As shown in FIG. 4, a stainless steel template 30 is placed on the end of a bone such as 32 in FIG. 5. Drill 34 rotates K-wire 36 to through locating template 30 to bore holes 40, 42, 44, 46 in the ends of bones 32, 48.

Indications

1. Indications which require joint arthroplastic procedures which include the following:

a) FLEXION contractures (rigid) of proximal interphalangeal joints (PIPJ's) and distal interphalangeal joints (DIPJ's) producing painful hammer and mallet digits;

b) DJD of joints;

c) rhuematiod arthritis requiring joint arthroplastics of MPJ's and PIPJ's (proximal interphalangeal joints);

d) gout;

e) infraction of bone; i.e., Freibergs; and f) joint subluxation with secondary degeneration.

Contraindications

Containdications are:

1. Patients who have a known sensitivity to poly-P-dioxanon;

2. infection;

3. poor bone stock (relative);

4. peripheral vascular disease;

5. neuropathy (a relative contraindication); and 6. these implants are not to be used in the first MPJ or interphalangeal joint (IPJ) of the hallux.

Technique

Figure 6:
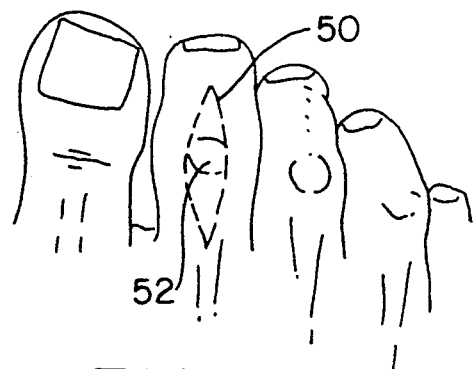
FIG. 6 is a plan view of a toe, showing a first step in the method of this invention.
Figure 7:
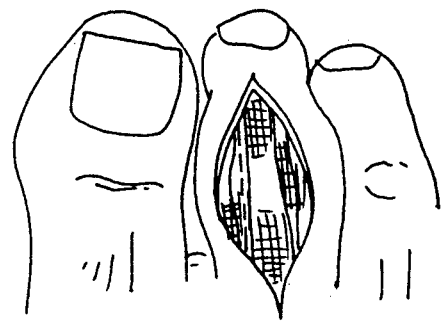
FIG. 7 is a similar view of the second step.
Figure 8:
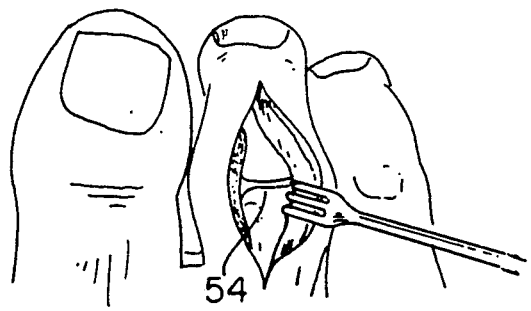
FIG. 8 is a similar view of another step.
Figure 9:
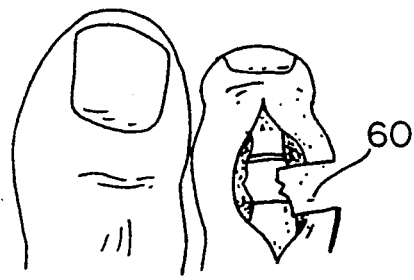
FIG. 9 is a similar view of another step.
Figure 10:
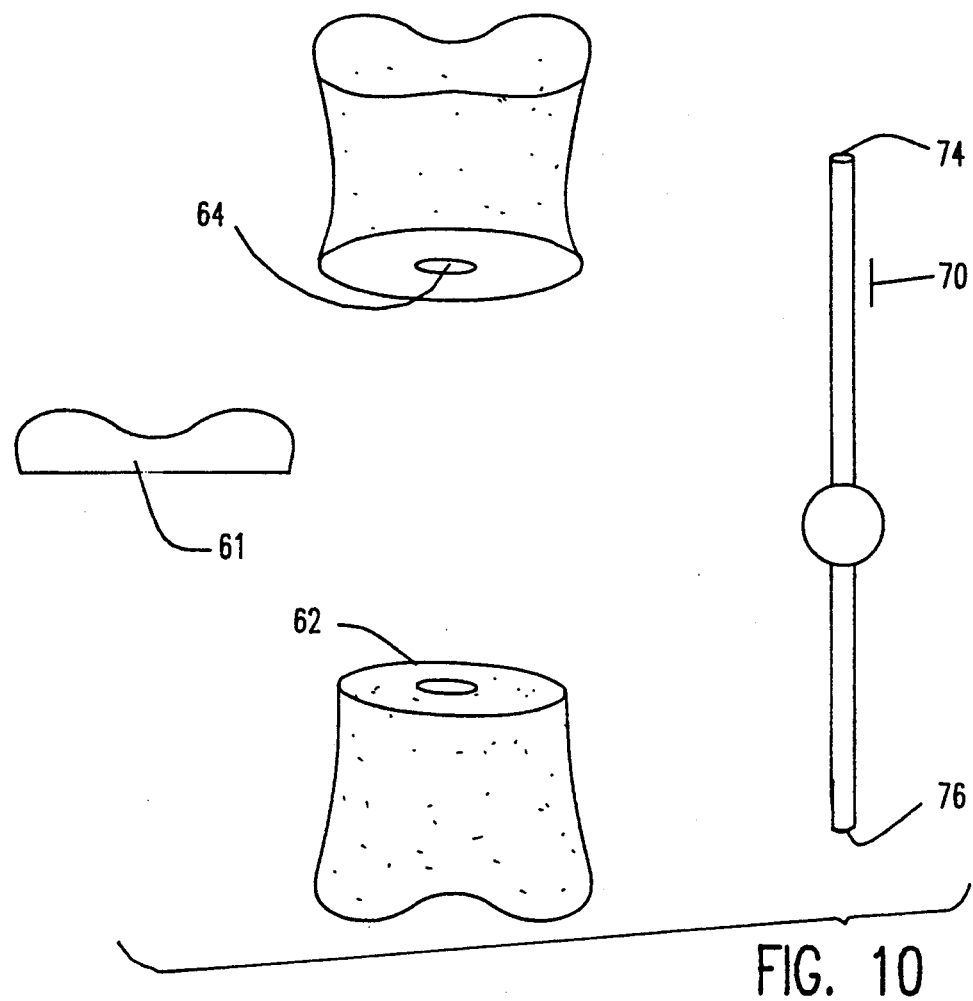
FIG. 10 is a view showing a pair of bones with a joint section therefrom and an implant of the present invention.

1. A dorsal linear incision 50 is placed over joint 52 [FIG. 6];

2. the extensor tendon is tenotomized [FIG. 7] and reflected [FIG. 8] exposing the joint capsule 54;

3. the capsule is incised transversely, exposing the head of the phalanx or metatarsal;

4. As in FIGS. 9, 10 the phalangeal head is resected (metatarsal) with a saggital saw 60 dorsal to plantarly for a Type I implant, Section 61 is removed;

5. holes are drilled proximally 62 and distally with 0.39-0.67 K-wire depending on size of implant as in FIG. 10; and 6. uni-stemmed implant 70 is fit into reamed holes 62, 64 with the central sphere 72 centered in the joint. The ends of the implant 74, 76 are cut to fit the proper size.

There are presently envisioned 2-3 sizes of this type, for use as appropriate.

Figure 11:
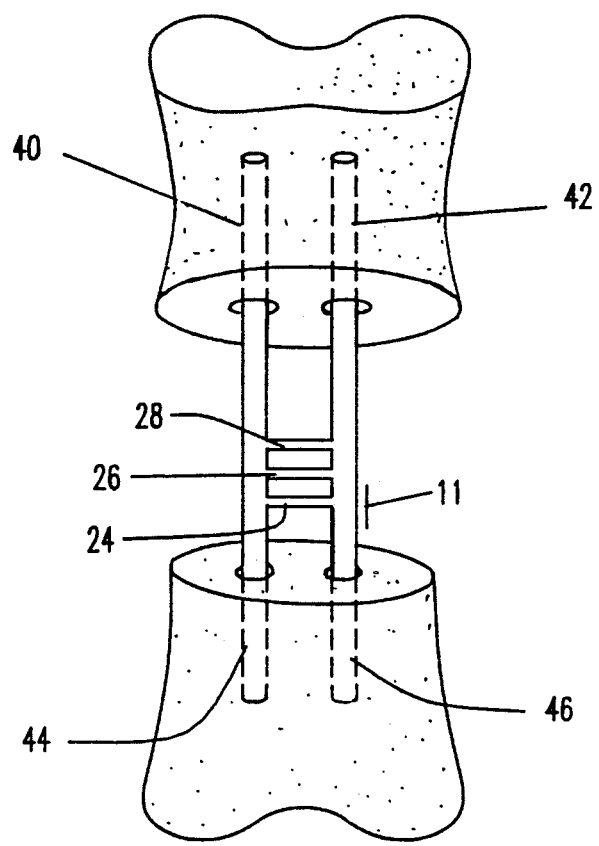
FIG. 11 is a view of a third embodiment of the present invention, located as intended between the bones, and ready to be slid into its intended position.

As in FIG. 11, for Type II implant, a template 30 is used to guide parallel drill holes 40, 42 made by 0.45" K-wires 36 (or manufacturing of 0.45-0.39" K-wires depending on the size of the implant).

7. A stainless steel guide pattern or cut-out 30 is used to cut two parallel holes into both bones. This implant will, in most cases, be used in the lesser MPJ's where more bone surface area is available.

8. As in FIGS. 3 and 11 the correct size implant 11 is used and inserted into the parallel drill holes 40, 42, 44, 46. This implant is cut to proper size centering the vertical "steps" 24, 26, 28 centrally (the focal or "stress" point of the joint).

Contrary to the teaching of Clemow, et al., supra, a tight fit between holes and implant shafts is not required, since it is intended to have fibrous tissues fill the space left between bones and shafts.

9. After placement, the stability and position of the toe is checked. Flexion and extension of the joint should not result in dislocation of the implant.

10. The tissue layers are then coapted as necessary. Tailoring of the extensor tendon is performed as needed.

11. The skin is coapted.

Post-op Care

1. The patient is allowed to ambulate freely after the second post operative day with post operative shoes; i.e., DARCO®, or REESE®.

2. Pre-operative antibiotic prophylaxis is recommended with the use of intravenous antibiosis; i.e., a regimen of ANCEF® one gram Intravenous piggy back every 8 hours, times 3 doses, or oxacillin one gram every 4-6 hours CALSO times 3 doses). Both with one dose prior to surgical intervention.

3. Due to the mildly radiopaque nature of the implant, post-operative X-rays are taken to check implant positioning, as well as toe position.

4. Sutures are removed in 2-3 weeks post-operatively, whereby the patient is slowly weened back to tennis shoes.

CONCLUSION

Introduced here is a concept utilizing an absorbable implant to achieve stability and maintain length without the complications of:

1) pin track infection; 2) biomaterial fatigue; 3) synovitis; 4) shard formation; or 5) the possibility of second surgery for implant removal.

Lastly, this in itself assures cost effectiveness and safety by avoiding the hazards of second surgery.

I claim:

1. A method of surgical correction for malformations of digits of a foot, said method comprising:

removing a section of a joint to expose bone ends;

said bone ends spaced apart from each other at a fibrous-tissue-forming distance greater than a distance suitable for knitting of said bone ends to each other with bone tissue;

providing in each of said bone ends hole means which comprise means for receiving shaft ends of an absorbable implant, said implant comprising:

shaft means for locating said bones in alignment to each other, and spacer means for maintaining said fibrous-tissue-forming distance between the bone ends, said implant consisting entirely of absorbable material;

placing said implant's shafts means into the hole means;

locating the bones on the shaft means with the bone ends at the spacer means at the spaced fibrous-tissue-forming distance, which fibrous-tissue-forming distance will encourage formation of fibrous tissue therebetween during a subsequent healing time;

appropriately closing the digit to allow healing; and leaving the implant in place, to be completely absorbed as it is replaced by fibrous tissue, which tissue forms an effective joint replacement.

2. A method according to claim 1, comprising boring the hole means through a template.

3. A method according to claim 2 in which the hole means comprises a pair of parallel holes and the template has a pair of open sleeves, wherein said method further comprises guiding the boring of the parallel holes in the bone ends, through said template.

4. A method according to claim 3 in which the shaft means comprises a pair of parallel shafts and the spacer means comprises a plurality of rungs therebetween.

5. An implant for correction of malformations of digits of a foot, said implant comprising:

shaft means for locating a pair of bones of a foot with respect to each other;

spacer means on said shaft means for maintaining a separation between said bones;

said separation being greater than a distance across which bone tissue is likely to grow during a healing process;

said spacer means being of a distance across which fibrous tissue is likely to form during a healing process; p1 said implant consisting of absorbable material means:

for absorption by the body, for complete replacement by fibrous tissue during the healing process, and for structural location of the bones during the healing process, said structural location function diminishing during said replacement by fibrous tissue.

6. An apparatus according to claim 5 in which the shaft means comprise a pair of parallel shafts; and the spacer means comprises a plurality of rungs between the shafts.

7. An apparatus according to claim 5 in which the absorbable material comprises poly-p-dioxanon.

8. An apparatus according to claim 6 in which the absorbable material comprises poly-p-dioxanone.

9. An apparatus according to claim 5 which the shaft means comprises a single shaft divided by a spherical bulge as the spacer means.

10. Apparatus according to claim 5 in which the shaft means comprises a pair of colinear shafts separated by a central spacer comprising a pair of rungs connected by a pair of parallel shafts, said shafts being of the desired separation distance.

* * * * *

UNITED STATES PATENT AND TRADEMARK OFFICE
CERTIFICATE OF CORRECTION

PATENT NO. : 5,207,712
DATED : May 4, 1993
INVENTOR(S) : Michael Cohen

It is certified that error appears in the above-identified patent and that said Letters Patent is hereby corrected as shown below:

Column 6, line 15, after "process;" change "pl" to line space and indentation for a new paragraph;

Column 6, line 33, after "5" insert --in--.

Signed and Sealed this

Eleventh Day of January, 1994

Attest:

BRUCE LEHMAN

*Attesting Officer*      *Commissioner of Patents and Trademarks*